(12) United States Patent
Kim

(10) Patent No.: US 9,863,747 B2
(45) Date of Patent: Jan. 9, 2018

(54) SYSTEM FOR INSPECTING, FIXING, OR SCREENING AMMUNITION

(71) Applicant: POONGSAN CORPORATION, Pyeongtaek-si, Gyeonggi-do (KR)

(72) Inventor: Woo Hyun Kim, Busan (KR)

(*) Notice: Subject to any disclaimer, the term of this patent is extended or adjusted under 35 U.S.C. 154(b) by 0 days.

(21) Appl. No.: 15/337,637

(22) Filed: Oct. 28, 2016

(65) Prior Publication Data

US 2017/0184384 A1   Jun. 29, 2017

(30) Foreign Application Priority Data

Dec. 28, 2015 (KR) .......................... 10-2015-0187039

(51) Int. Cl.
  *B07C 5/00* (2006.01)
  *F42B 35/02* (2006.01)
  (Continued)

(52) U.S. Cl.
  CPC .............. *F42B 35/02* (2013.01); *B07C 5/342* (2013.01); *B07C 5/34* (2013.01); *G01N 21/00* (2013.01)

(58) Field of Classification Search
  CPC ... B07C 5/34; B07C 5/342; B07C 5/36; F42B 35/00; F42B 35/02; G01N 21/00
  (Continued)

(56) References Cited

U.S. PATENT DOCUMENTS 1,602,334 A * 10/1926 Candee .................. F42B 33/001
                                                                209/698
2,859,871 A * 11/1958 Harlow .................. G01R 31/18
                                                                209/571
(Continued)

FOREIGN PATENT DOCUMENTS

KR        10-0918529        9/2009
KR     10-2012-0071955      7/2012
(Continued)

OTHER PUBLICATIONS

English translation of 10-1390569.
(Continued)

*Primary Examiner* — Joseph C Rodriguez
*Assistant Examiner* — Kalyanavenkateshware Kumar
(74) *Attorney, Agent, or Firm* — Antonio Ha & U.S. Patent, LLC

(57) ABSTRACT

A system for inspecting, fixing, or screening ammunition comprises an ammunition conveying track, a plurality of ammunition trays arranged on an outer surface of the ammunition conveying track, an ammunition inspector disposed at right and left sides of the ammunition conveying track, an ammunition fixer disposed downstream of the ammunition inspector at right and left sides of the ammunition conveying track, and an ammunition discharger disposed at an end point of the upper portion of the ammunition conveying track, ammunition cartridges being sequentially discharged through the ammunition fixer and the ammunition discharger, wherein at least one of the ammunition inspector and the ammunition fixer includes ammunition-shaped chambers and actuators, wherein the ammunition cartridges placed on the ammunition trays are moved horizontally and inserted into the chambers, and wherein the actuators horizontally move the ammunition cartridges inserted in the chambers back to the ammunition trays.

2 Claims, 9 Drawing Sheets
(9 of 9 Drawing Sheet(s) Filed in Color)

(51) Int. Cl.
*B07C 5/342* (2006.01)
*G01N 21/00* (2006.01)
*B07C 5/34* (2006.01)

(58) Field of Classification Search
USPC ...... 209/552, 576, 577, 651; 102/501; 86/24
See application file for complete search history.

(56) References Cited

U.S. PATENT DOCUMENTS

| | | | | |
|---|---|---|---|---|
| 2,897,964 A | * | 8/1959 | Foster | ............ F42B 35/02 |
| | | | | 209/549 |
| 3,019,688 A | * | 2/1962 | Hunt | ............ F42B 33/002 |
| | | | | 100/99 |
| 4,882,972 A | | 11/1989 | Raymond | |
| 4,923,066 A | * | 5/1990 | Ophir | ............ F42B 35/00 |
| | | | | 209/538 |

FOREIGN PATENT DOCUMENTS

| | | |
|---|---|---|
| KR | 10-2014-0001013 | 1/2014 |
| KR | 10-1390569 | 5/2014 |
| KR | 10-2014-0070908 | 6/2014 |

OTHER PUBLICATIONS

English translation of 10-2014-0070908.
English translation of 10-0918529.
English translation of 10-2012-0071955.
English translation of 10-2014-0001013.

* cited by examiner

SYSTEM FOR INSPECTING, FIXING, OR SCREENING AMMUNITION

CROSS-REFERENCE TO RELATED APPLICATIONS

This patent application claims priority under 35 U.S.C. §119 to Korean Patent Application No. 10-2015-0187039, filed on Dec. 28, 2015, in the Korean Intellectual Property Office, the disclosure of which is incorporated by reference herein in its entirety.

TECHNICAL FIELD

Embodiments of the present disclosure concern automated inspection, fixation, and screening of ammunition, and more specifically, to systems capable of inspecting ammunition, fixing the ammunition using inspected results and screening the ammunition using inspected or fixed results.

DISCUSSION OF RELATED ART

There are various manual or automatic ways for inspecting, sorting, or repairing defective ammunition cartridges. FIG. 1 illustrates a conventional manual ammunition inspector for the purposes. However, such conventional manual systems cannot respond to the demand for mass production or processing. Although a few automated systems have been introduced for sorting, inspecting, or fixing ammunition, they simply carry out their individual tasks discretely rather than collaborating together stage-to-stage on the same processing line. Therefore, a need exists for a more streamlined approach to inspecting, repairing, and screening ammunition in the same processing line by allowing information at a prior stage to be used in subsequent stage(s).

SUMMARY

According to an embodiment of the present disclosure, a system for inspecting, fixing, or screening ammunition comprises an ammunition conveying track, a plurality of ammunition trays arranged on an outer surface of the ammunition conveying track, an ammunition inspector disposed at right and left sides of an upper portion of the ammunition conveying track, an ammunition fixer disposed downstream of the ammunition inspector at right and left sides of the upper portion of the ammunition conveying track, and an ammunition discharger disposed at an end point of the upper portion of the ammunition conveying track. Ammunition cartridges may be sequentially discharged through the ammunition fixer and the ammunition discharger. At least one of the ammunition inspector and the at fixer may include ammunition-shaped chambers and actuators. The ammunition cartridges placed on the ammunition trays may be moved horizontally and inserted into the chambers. The actuators horizontally may move the ammunition cartridges inserted in the chambers back to the ammunition trays.

The ammunition inspector includes a plurality of inspecting chambers and a plurality of inspecting actuators, and the ammunition fixer includes a plurality of fixing chambers and a plurality of fixing actuators. The number of the inspecting chambers may be the same as the number of the fixing chambers, and the number of the inspecting actuators may be the same as the number of the fixing actuators, and wherein the fixing actuators are operated as per information obtained by the inspecting actuators arranged in the ammunition inspector in the same order as the fixing actuators in the ammunition fixer.

The system may further comprise an ammunition screener disposed downstream of the ammunition fixer at the right or left side of the upper portion of the ammunition conveying track.

The ammunition screener may include a plurality of screening actuators that are of the same number as the inspecting actuators. The screening actuators may be operated as per the information obtained by the inspecting actuators arranged in the ammunition inspector in the same order as the screening actuators in the ammunition screener.

The screening actuators may be operated as per fixing information obtained by the fixing actuators arranged in the ammunition fixer in the same order as the screening actuators in the ammunition screener.

The inspecting chambers and the fixing chambers respectively may include returning actuators returning inspected or fixed ammunition cartridges to the ammunition trays. Actuating rods of the returning actuators, respectively, may push off heads of the ammunition cartridges through the inspecting chambers or the fixing chambers.

The measurement information may include an insertion depth into a particular inspecting chamber corresponding to as particular inspecting actuator, and the fixing information may include an operation pressure of a particular fixing actuator or an insertion depth into a particular fixing chamber corresponding to the particular fixing actuator.

BRIEF DESCRIPTION OF THE DRAWINGS

The patent application file contains at least one or more drawings executed in color. Copies of this patent application publication with color drawings will be provided by the Office upon request and payment of the necessary fee.

A more complete appreciation of the present disclosure and mans of the attendant aspects thereof will be readily obtained as the same becomes better understood by reference to the following detailed description when considered in connection with the accompanying drawings, wherein.

DETAILED DESCRIPTION OF EXEMPLARY EMBODIMENTS

Hereinafter exemplary embodiments of the present disclosure will be described in detail with reference to the accompanying drawings. The same reference denotations may be used to refer to the same or substantially the same elements throughout the specification and the drawings. The present disclosure, however, may be modified in various different ways, and should not be construed as limited to the embodiments or by the terminology set forth herein. As used herein, the singular forms "a," "an," and "the" are intended to include the plural forms as well, unless the context clearly indicates otherwise. It will be understood that when an element or layer is referred to as, being "on," "connected to," "coupled to," or "adjacent to" another element or layer, it can be directly on, connected, coupled, or adjacent to the other element or layer, or intervening elements or layers may be present.

Figure 1:
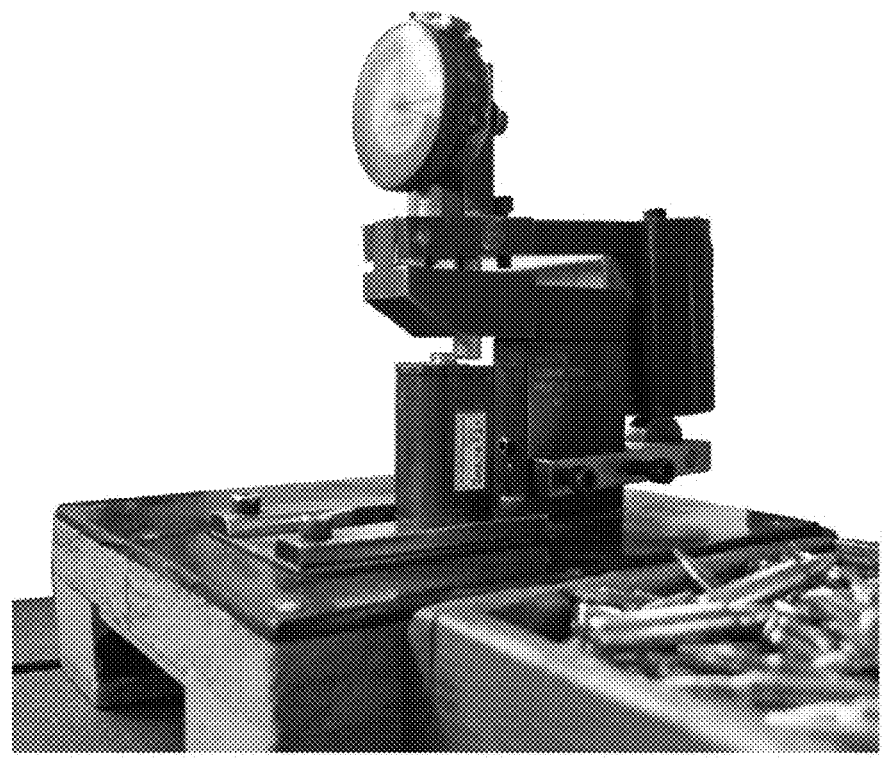
FIG. 1 is a view illustrating a manual ammunition inspector according to the related art.
Figure 2:
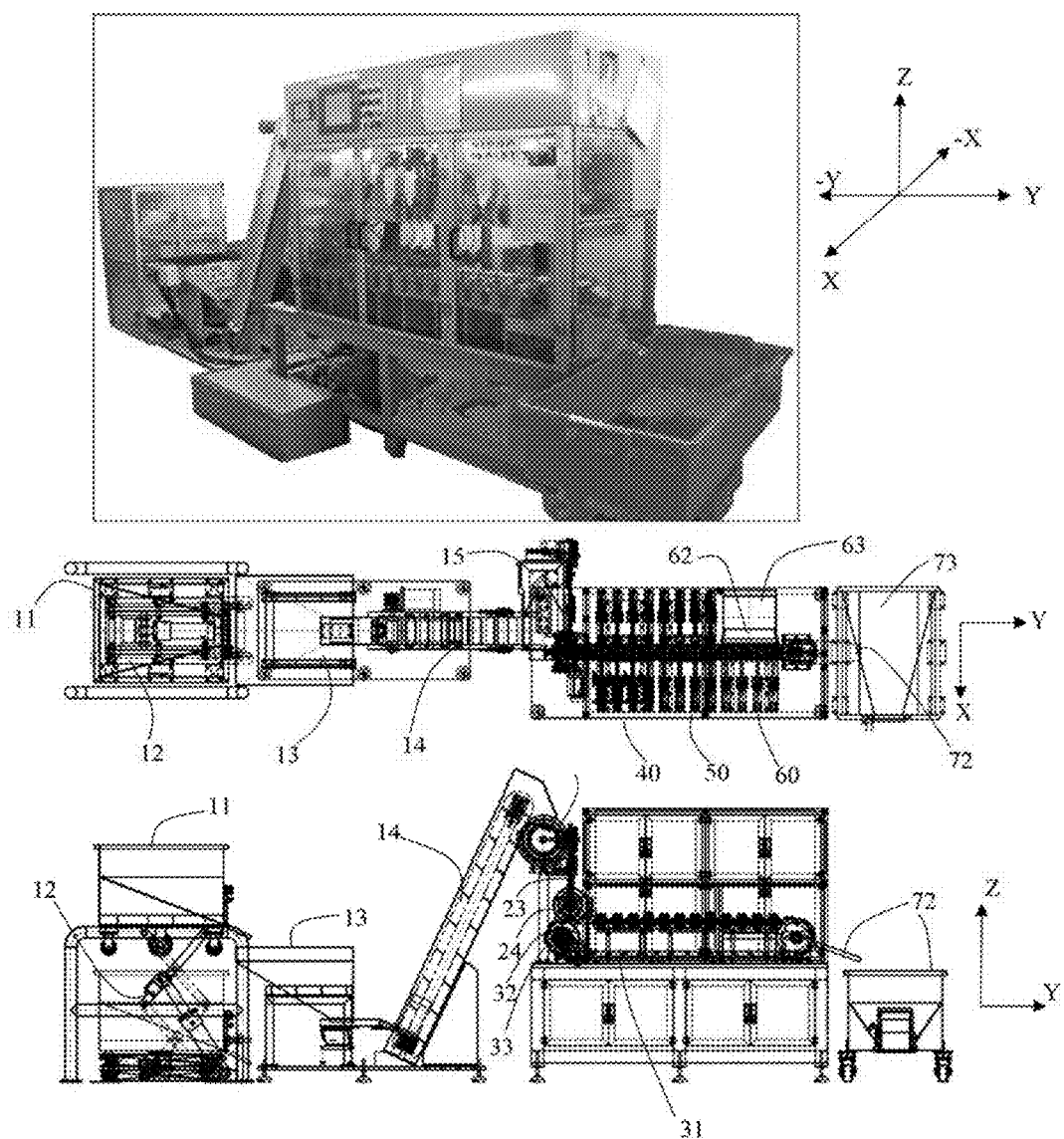
FIG. 2 illustrates an overall configuration of a system for inspecting, fixing, or screening ammunition according to an embodiment of the present disclosure.
Figure 3:
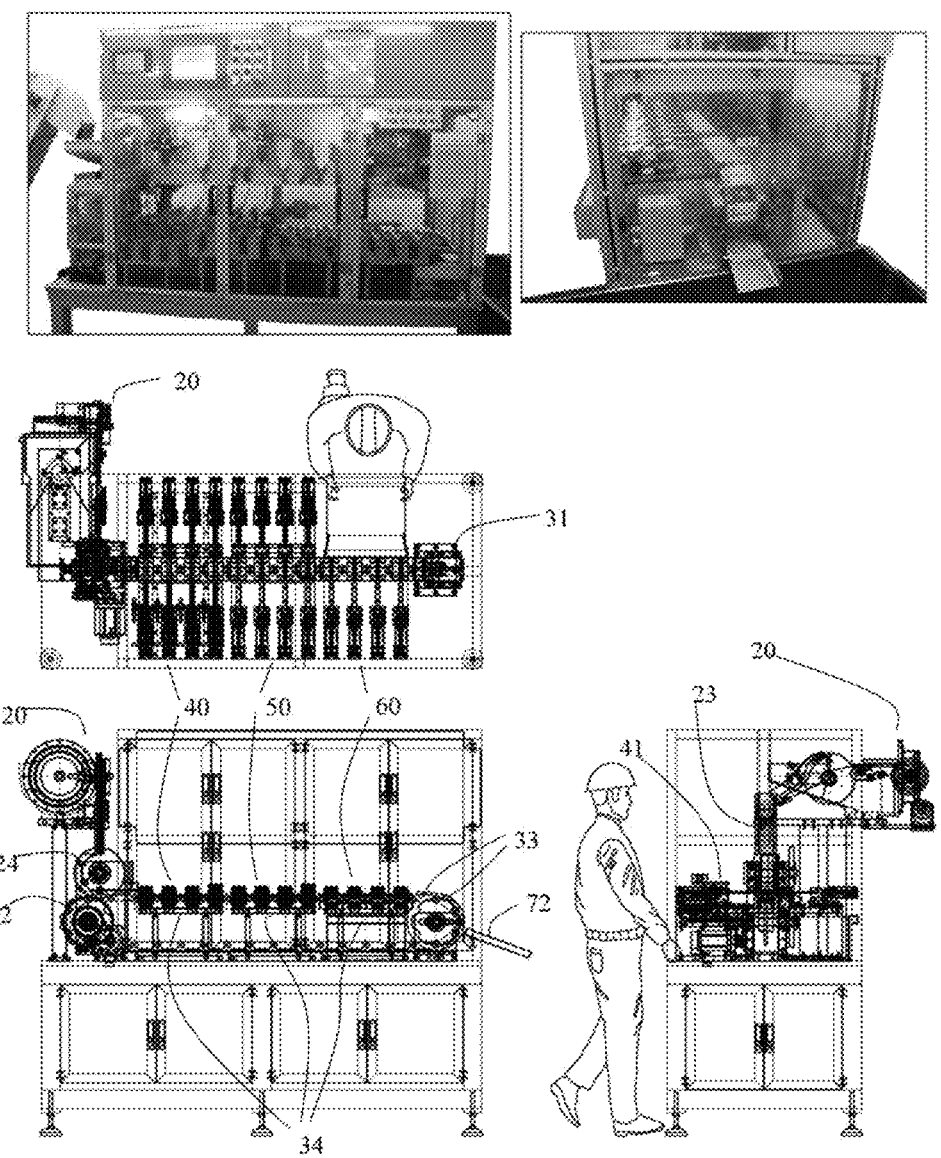
FIG. 3 illustrates a configuration of a body of a system for inspecting, fixing, or screening ammunition according to an embodiment of the present disclosure.
Figure 4:
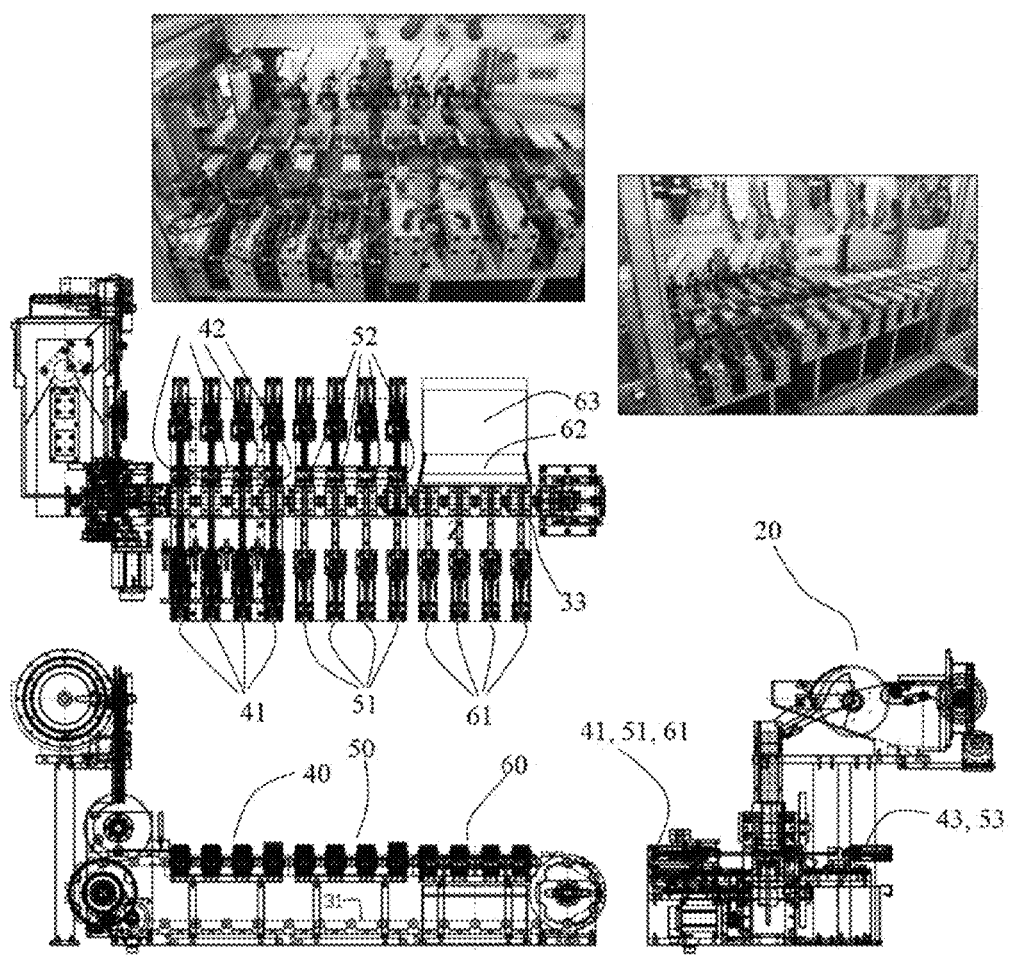
FIG. 4 illustrates a configuration of a main portion of a system for inspecting, fixing, or screening ammunition according, to an embodiment of the present disclosure.
Figure 5:
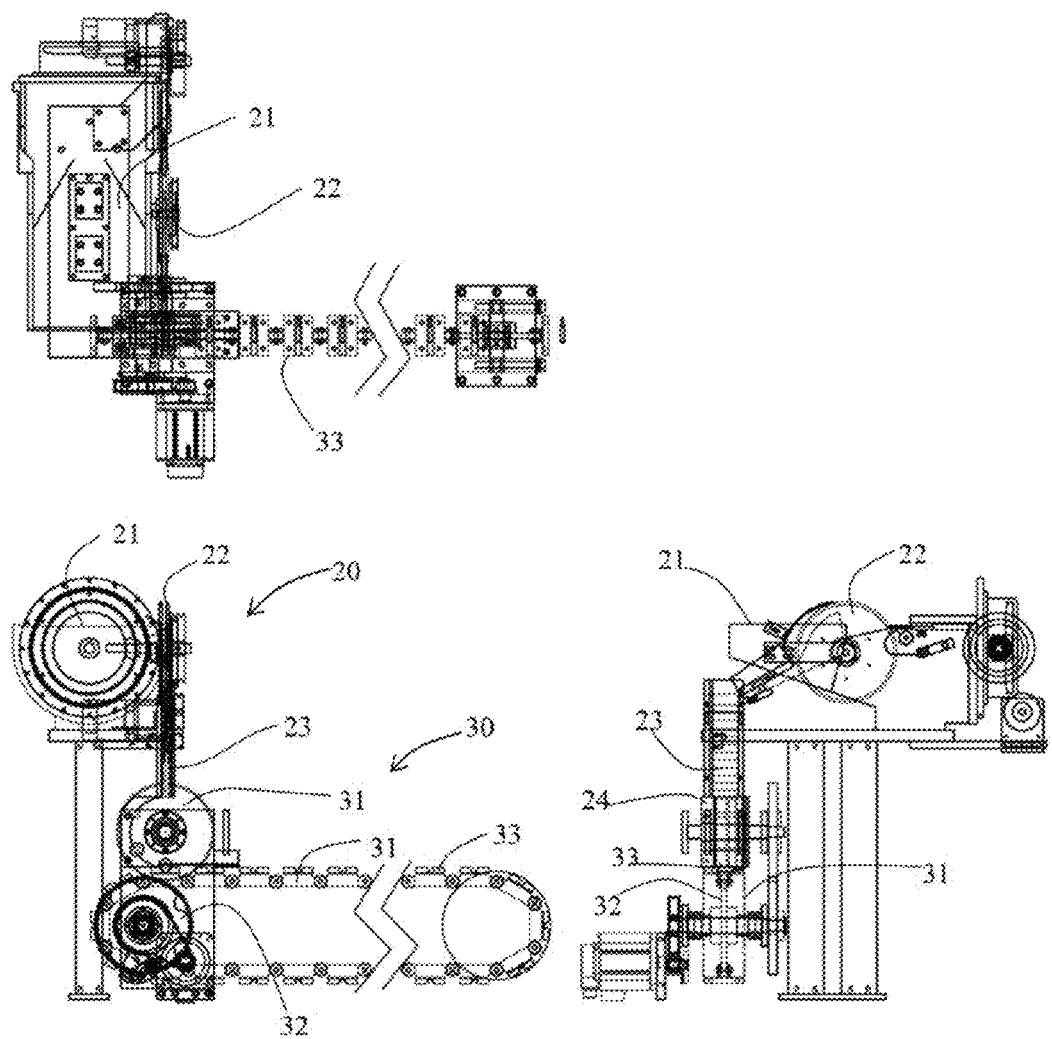
FIG. 5 illustrates an ammunition feeder and an ammunition conveyer of a system for inspecting, fixing, or screening ammunition according to an embodiment of the present disclosure.

FIG. 2 illustrates an overall configuration of a system for inspecting, fixing, or screening ammunition according to an embodiment of the present disclosure. FIG. 3 illustrates a configuration of a body of a system for inspecting, fixing, or screening ammunition according to an embodiment of the present disclosure. FIG. 4 illustrates a configuration of a main portion of a system for inspecting, fixing, or screening ammunition according to an embodiment of the present disclosure. FIG. 5 illustrates an ammunition feeder and an ammunition conveyer of a system for inspecting, fixing, or screening ammunition according to an embodiment of the present disclosure.

Referring to FIGS. 2 to 4, the system for inspecting, fixing, or screening ammunition (hereinafter, simply referred to as 'the system') may include a plurality of working modules. The working modules may include an ammunition injector 10, an ammunition feeder 20, an ammunition conveyer 30, an ammunition inspector 40, an ammunition fixer 50, an ammunition screener 60. and an ammunition discharger 70.

Tasks may be sequentially performed in the order of the ammunition injector 10, the ammunition feeder 20, the ammunition conveyer 30, and the ammunition discharger 70. The ammunition inspector 40, the ammunition fixer 50, and the ammunition screener 60 may perform their respective tasks in the ammunition conveyer 30.

The working modules may follow common references for operational directions, for example, X, Y, and Z directions as indicated in FIG. 2. Ammunition cartridges may be conveyed along at track (e.g., the ammunition conveying track 31 included in the ammunition conveyor 30) in a front-rear direction (erg., Y direction of FIG. 2) of the system. Actuators included in the working modules may operate in a left-right direction (e.g., X or its opposite (−X) direction) of the system. Tasks or processing by the actuators may be performed on an upper portion (also referred to herein as an upper track) of the track (e.g., the ammunition conveying track 31) which moves in the front-rear direction (e.g., Y direction of FIG. 2). A lower portion (also referred to herein as a lower track) of the track (e.g., the ammunition conveying track 31) moves in a rear-front direction (e.g., −Y direction of FIG. 2) with no ammunition cartridges loaded thereon.

The ammunition injector 10 may correspond to a start point for a process. The ammunition injector 10 may include a basket 11, a basket lifter 12, a lower hopper 13, and a bucket conveyer 14. The basket lifter 12 lifts up the basket 11 containing ammunition cartridges and tilts to pour the ammunition cartridges into the lower hopper 13. The ammunition cartridges are conveyed from the lower hopper 13 to the ammunition feeder 20 by the bucket conveyer 14.

The ammunition discharger 70 is disposed at an end point of the upper track of the ammunition conveying track 31 and gathers ammunition cartridges that are discharged through the ammunition fixer 50 and that are not screened out by the ammunition screener 60. The ammunition discharger 70 may in a screen-in outlet 72 and a screen-in basket 73.

Referring to FIG. 5, the ammunition feeder 20 includes an upper hopper 21, a sorter 22, an ammunition feeding magazine 23, and an ammunition feeding wheel 24. A handle provided in the upper hopper 21 picks up ammunition cartridges one by one while revolving the ammunition cartridges. The ammunition cartridges picked up by the handle are revolved along a circular track on the inner circumferential surface of the upper hopper 21, are sorted in a row by the sorter 22 near an end point of the upper hopper 21 and are supplied via the ammunition feeding magazine 23 to the ammunition feeding wheel 24. The sorter 22 may be structured to guide each ammunition cartridge so that the casing-side of the ammunition cartridge first drops through a hole shorter than the ammunition cartridge.

The ammunition conveyer 30 includes an ammunition conveying track 31 and a driving sprocket 32. The ammunition conveying track 31 may be a Caterpillar track on which ammunition trays 33 are arranged on the outer surface of the ammunition conveying track 31. The driving sprocket 32 simultaneously rotates the ammunition conveying track 31 and the ammunition feeding wheel 24, allowing ammunition cartridges to be loaded one by one from the ammunition feeding wheel 24 onto the, ammunition trays 33, respectively.

Thus, the ammunition cartridges are arranged at predetermined intervals in the same direction on the upper portion of the ammunition conveying track 31 and are conveyed from a front portion of the ammunition conveying track 31 to a rear portion thereof (e.g., in the Y direction).

Figure 6:
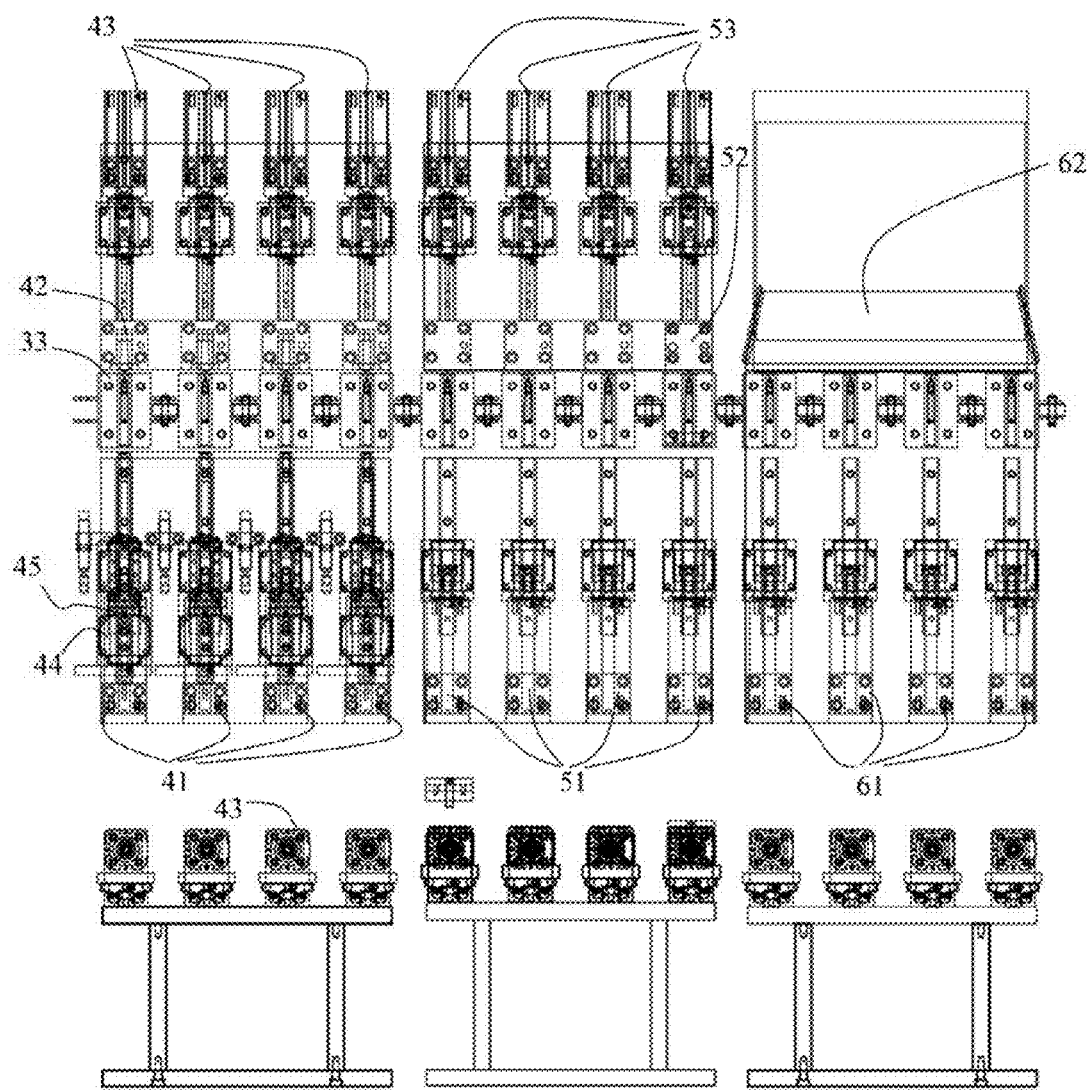
FIG. 6 illustrates actuators performing a task on an ammunition conveyer track of a system for inspecting, fixing, or screening ammunition according to an embodiment of the present disclosure.
Figure 7:
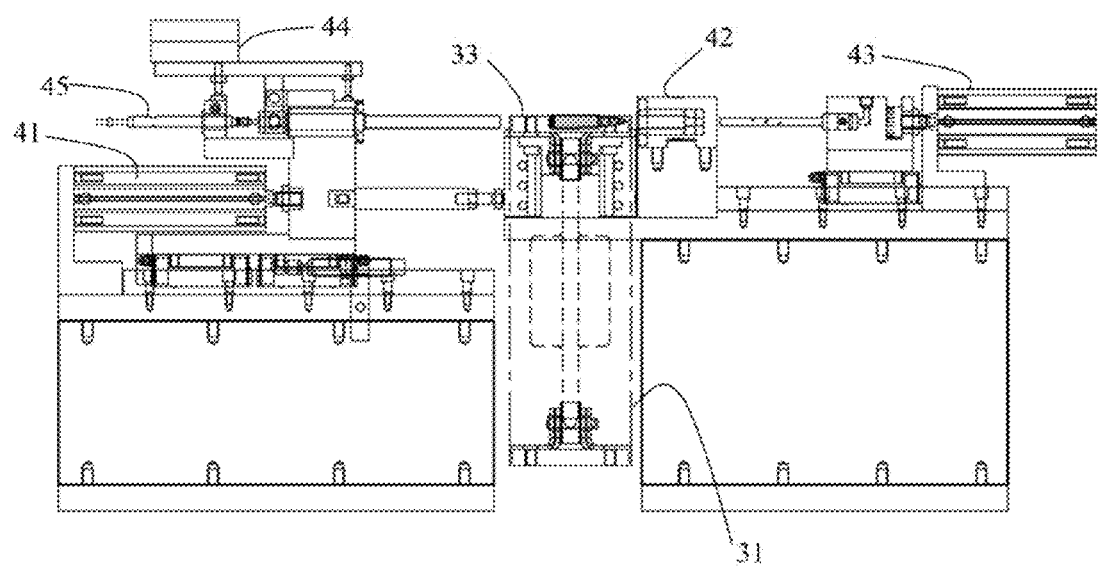
FIG. 7 is a view illustrating an ammunition inspector of a system for inspecting, fixing, or screening ammunition according to an embodiment of the present disclosure.
Figure 8:
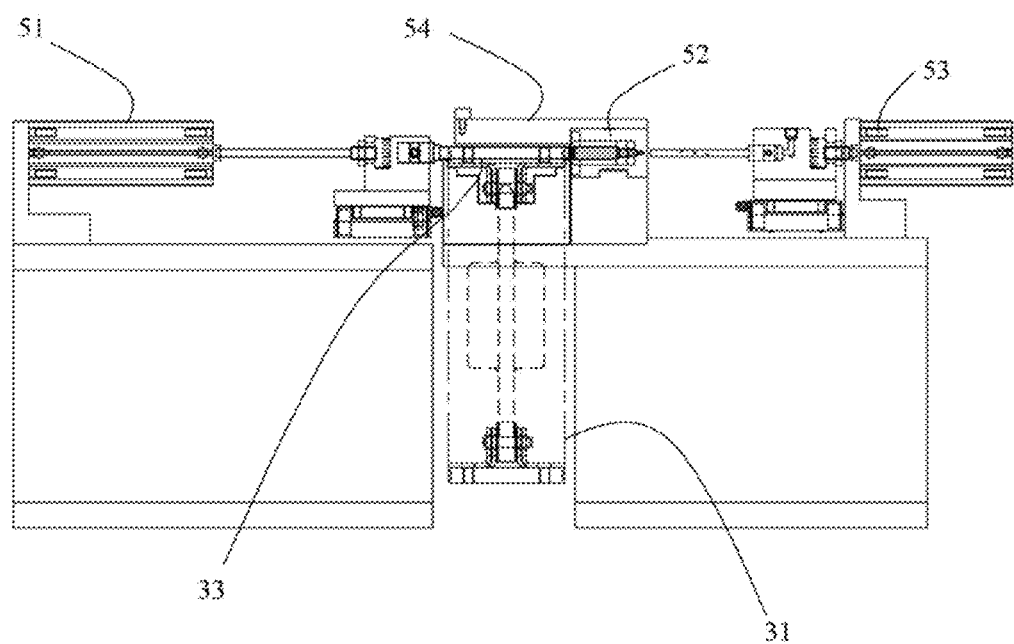
FIG. 8 is a view illustrating an ammunition fixer of a system for inspecting, fixing, or screening ammunition according to an embodiment of the present disclosure.
Figure 9:
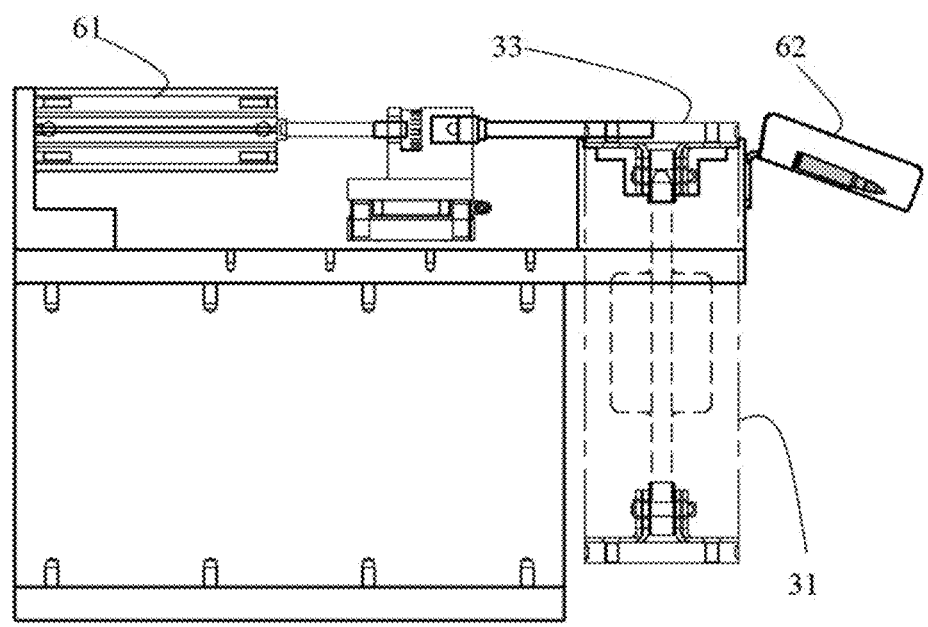
FIG. 9 is a view illustrating an ammunition screener for a system for inspecting, fixing, or screening ammunition according to an embodiment of the present disclosure.

FIG. 6 illustrates actuators performing a task on an ammunition conveyer track of a system for inspecting, fixing, or screening ammunition according to an embodiment of the present disclosure. FIG. 7 is a view illustrating an ammunition inspector of a system for inspecting, fixing or screening ammunition according to an embodiment of the present disclosure. FIG. 8 is a view illustrating an ammunition fixer of a system for inspecting, fixing, or screening ammunition according to an embodiment of the present disclosure. FIG. 9 is a view illustrating an ammunition screener for a system for inspecting, fixing, or screening ammunition according to an embodiment of the present disclosure.

Although FIGS. 6 to 9 illustrate three groups of actuators, each group including four actuators, this is merely an example, and embodiments of the present disclosure are not limited thereto. The number of actuator groups or the number of actuators included in each actuator group may be varied as necessary. For example the system may include three groups of actuators, each group having five actuators, or our groups each having four actuators.

For example, when ammunition cartridges are categorized into unfixed, flawless ones as a first grade (e.g., best-quality), fixable ones as a second grade (e.g., high-quality), and unfixable ones as a third grade (e.g., low-quality), the system may include four actuator groups each including four actuators, with two of the actuator groups allocated to the ammunition screener 60. In this case, the ammunition inspector 40 and the ammunition fixer 50 each may include one four-actuator group, and the ammunition screener 60 may include two four-actuator groups.

The ammunition inspector 40 is disposed at left and right sides (e.g., in the X or −X direction) of the upper portion of the ammunition conveying track 31. The ammunition inspector 40 includes a plurality of inspecting chambers 42 and a plurality of inspecting actuators 41. The number of it chambers 42 may be the same as the number of inspecting actuators 41.

When ammunition cartridges are inserted from the ammunition trays 33 into the inspecting chambers 42, electronic sensors, also referred to as electronic micrometers or including the probes 45, may obtain predetermined information, such as the overall length, contour, and shoulder length of the ammunition cartridges, to determine whether the ammunition cartridges need to be fixed. The predetermined information obtained by the ammunition inspector 40 may be referred to herein as 'measurement information."

When the ammunition cartridge is determined based on the obtained information to be required to be fixed, the ammunition cartridge may be fixed by the ammunition fixer 50 at a subsequent stage. Alternatively, When the ammunition cartridge is determined based on the obtained information to be not required to be fixed, the ammunition cartridge may skip the fixing process by the ammunition fixer 50.

The inspecting chambers 42 each are formed to have an internal shape similar to the shape of the ammunition cartridge and are arranged so that the ammunition cartridges respectively placed on the ammunition trays 33 may be moved horizontally and inserted into the inspecting chambers 42.

The inspecting actuators 41 each include an air pressure cylinder and an air pressure rod. Similar to the inspecting actuators 41, the actuators included in other working modules, e.g., returning actuators 43, fixing actuators 51, returning actuators 53, and screening actuators 61, each may also include an air pressure cylinder and an air pressure rod.

The ammunition cartridges are slightly inserted into the inspecting chambers 42 by the inspecting actuators 41 and are then further inserted by standard load mechanisms (weights 44 and probes 45) coupled to upper portions of the air pressure rods of the inspecting actuators 41 while predetermined information is obtained by the probes 45. The predetermined information may include an insertion depth, of an ammunition cartridge into a particular inspecting chamber 42 corresponding to a particular inspecting actuator 41.

The ammunition fixer 50 may be a downstream working, module that is next to the ammunition inspector 40 and is disposed at right and left sides (e.g., in the X or −X direction) of the upper portion of the ammunition conveying track 31. For example, the ammunition cartridges having passed through the ammunition inspector 40 may be subjected to processing (e.g., fixation) by the ammunition fixer 50.

The ammunition fixer 50 may include the same number of fixing chambers 52 as the number of inspecting chambers 42 and the same number of fixing actuators 51 as the number of inspecting actuators 41.

The fixing actuators 51 are operated as per the information obtained by the probes 45 and inspecting actuators 41 arranged in the same order, as the fixing actuators 51 in the ammunition fixer 50. For example, whether to operate a fixing actuator 51 may be determined based on the obtained information. For example, when an ammunition cartridge inspected by an inspecting actuator 41 is determined based on the obtained information to be required to be fixed, the ammunition cartridge may be fixed by a fixing actuator 51 corresponding in order to the inspecting actuator 41.

For example, the fixing actuators 51, respectively, correspond in order to the inspecting actuators 41. When the ammunition cartridge processed by a first one of the inspecting actuators 41 is determined to be fixed by the probe 42 associated with the first inspecting actuator 41, a first fixing actuators 51, which corresponds to the first inspecting actuator 41, may be operated to fix the ammunition cartridge according to the information obtained by the probe 42 associated with the first inspecting actuator 41. When the ammunition cartridge processed by a second one of the inspecting actuators 41 is determined to be fixed by the probe 4 associated with the second inspecting actuator 41, a second fixing actuators 51, which corresponds to the second inspecting actuator 41, may be operated to fix the ammunition cartridge according to the information obtained by the probe 42 associated with the second inspection actuator 41. When the ammunition cartridge processed by a third one of the inspecting actuators 41 is determined to be fixed by the probe 42 associated with the third inspecting actuator 41, a third fixing actuators 51, which corresponds to the third inspecting actuator 41, may be operated to fix the ammunition cartridge according to the information obtained by the probe 42 associated with the third inspecting actuator 41. When the ammunition cartridge processed by a fourth one of the inspecting actuators 41 is determined to be fixed by the probe 42 associated with the fourth inspecting actuator 41, a fourth fixing actuators 51, which corresponds to the fourth inspecting actuator 41, may be operated to fix the ammunition cartridge according to the information obtained by the probe 42 associated with the fourth inspecting actuator 41.

As such, the measurement information obtained by the ammunition inspector 40 may be used to operate or determine whether to operate the ammunition fixer 50.

The ammunition fixer 50 may further include tray covers 54 that may be installed over the chambers 42 and 52 depending on the speed of the inspecting actuators 41 or fixing actuators 51. The tray covers 54 may prevent the ammunition cartridges from escaping off the ammunition trays 33 and resultant failure to be inserted in position into the holes of the chambers 42 and 52 when forced at high speed or pressure.

Fixable ammunition cartridges are first inserted into the fixing chambers 52 and are then pressurized and hammered in the air pressure cylinders of the fixing actuators 51 to be further inserted into the fixing chambers 52 so that the ammunition cartridges fit their desired shape or conform to predetermined standards. Fixing information on an ammunition cartridge may include an operation pressure of a particular fixing actuator 51 and an insertion depth of the ammunition cartridge into a particular fixing chamber 52 corresponding to the particular fixing actuator 51.

The ammunition inspector 40 may further include returning actuators 43 that may return inspected or measured ammunition cartridges to their respective corresponding ammunition trays 33. The ammunition fixer 50 may further include returning actuators 53 that may return fixed ammunition cartridges to their respective corresponding ammunition trays 33. The respective actuating rods (e.g., the above-described air pressure rods of the returning actuators 43 and 53 may horizontally push the bullets of the ammunition cartridges or their heads through the chambers 42 and 52 back to the ammunition trays 33. The returning actuators 43 and their respective corresponding inspecting actuators 44 may be positioned at two opposite sides, e.g., right and left sides (e.g., in the X or −X direction), of the upper portion of the ammunition conveying track 31. The returning actuators 53 and their respective corresponding fixing actuators 51 may be positioned at two opposite sides, e.g., right and left sides, (e.g., in the X or −X direction), of the upper portion of the ammunition conveying track 31.

The ammunition screener 60 is disposed downstream of the as fixer 50 and next to the ammunition fixer 50 at a right or left side (e.g., in the X or −X direction) of the upper portion of the ammunition conveying track 31. For example, ammunition cartridges processed by the ammunition fixer 50 undergo processing by the ammunition screener 60.

For example, whether to operate a screening actuator 61 may be determined based on the measurement information, the fixing information, or a result of the fixation by the fixing actuator 51. For example, when art ammunition cartridge inspected by an inspecting actuator 41 is determined based on the measurement information to be not required to be fixed, the ammunition cartridge may pass through the ammunition fixer 50 and the ammunition screener 60 to the screen-in outlet 72 and is gathered by the screen-in basket 73 without the operation of any actuator in the ammunition fixer 50 and the ammunition screener 60. For example, when the shape of an ammunition cartridge fixed by a fixing actuator 51 is determined based on the result of fixation or fixing information to be within a predetermined acceptable range, the ammunition cartridge is not processed by a screening actuator 61 but carried to the screen-in outlet 72 and gathered in the screen-in basket 73.

The ammunition screener 60 may include the same number of screening actuators 61 as the number of inspecting actuators 41. The screening actuators 61 are operated as per the measurement information obtained by the probes 45 and inspecting actuators 41 arranged in the ammunition inspector 40 in the same order as the screening actuators 61 in the ammunition screener 60 or as per fixing information obtained by the fixing actuators 51 arranged in the ammunition fixer 50 in the same order as the screening actuators 61 in the ammunition screener 60 to thereby selectively discharge ammunition cartridges to a screen-out outlet 62. The screen-out outlet 62 may be positioned at an opposite side of the screening actuators 61 with respect to the upper portion of the ammunition conveying track 31.

For example, the screening actuators 61, respectively correspond in order to the inspecting actuators 41, or the screening actuators 61, respectively, correspond in order to the fixing actuators 51. For example, the ammunition cartridge processed by a first inspecting actuator 41 or first fixing actuator 51 may be selectively discharged to the screen-out outlet 62 by a first screening actuator 61 according to the information obtained by the first inspecting actuator 41 or the fixing information obtained by the first fixing actuator 51; the ammunition cartridge processed by a second inspecting actuator 41 or second fixing actuator 51 may be selectively discharged to the screen-out outlet 62 by a second screening actuator 61 according to the information obtained by the second inspecting actuator 41 or the fixing information obtained by the second fixing actuator 51; the ammunition cartridge processed by a third inspecting actuator 41 or third fixing actuator 51 may be selectively discharged to the screen-out outlet 62 by a third screening actuator 61 according to the information obtained by the third inspecting actuator 41 or the fixing information obtained by the third fixing actuator 51; and the ammunition cartridge processed by a fourth inspecting actuator 41 or fourth fixing actuator 51 may be selectively discharged to the screen-cast outlet 62 by a fourth screening actuator 61 according to the information obtained by the fourth inspecting actuator 41 or the fixing information obtained by the fourth fixing actuator 51.

Although FIG. 6 illustrates an example in which the ammunition screener 60 includes, one group of screening actuators 61 (four screening actuators 61), embodiments of the present disclosure are not limited thereto, and the ammunition screener 60 may include one or more four-screening actuator groups. As an example, the ammunition screener 60 may include two four-screening actuator groups, e.g., a first group of screening actuators and a second group of screening actuators. In this case, defective ammunition cartridges required to be fixed may skip the processing by the ammunition fixer 50 and are screened out by the second group of screening actuators. By doing so, a number of ammunition cartridges may be classified into more diverse types.

As described above, measurement information obtained by the ammunition inspector 40 in the system may be used to operate or determine whether to operate the ammunition fixer 50, and measurement information obtained by the ammunition inspector 40 or fixing information obtained by the ammunition fixer 50 may be used to operate or determine whether to operate the ammunition screener 60, allowing for continuous inspection, fixation, and sorting of ammunition cartridges.

The analysis, interpretation, or determination of the measurement information, the fixing information, and the result of fixation, which are collectively referred to as control information herein, or determination as to as to whether to operate each component in the system may be performed by a controller or processor (not shown) connected or coupled with the system. The control information may be stored in a database or storage device (not shown). The storage device may store instructions or commands executed to enable the controller or processor to perform at least one operation including operating an ammunition conveying track 31, operating a plurality of ammunition trays 33 arranged on an outer surface of the ammunition conveying track, operating an ammunition inspector 40 disposed at right and left sides of an upper portion of the ammunition conveying track 31, operating an ammunition fixer 50 disposed downstream of the ammunition inspector 40 at right and left sides of the upper portion of the ammunition conveying track 31, operating an ammunition discharger 60 disposed at an end point of the upper portion of the ammunition conveying track 31, and the ammunition cartridges placed on the ammunition trays are moved horizontally and inserted into the chambers, and to enable the actuators horizontally to horizontally move the ammunition cartridges inserted in the chambers back to the ammunition trays 33.

The control information may in size and dimension information on the ammunition cartridges, information on whether the ammunition cartridges meet predetermined references or standards, and strength of a force that is to be applied to the ammunition cartridge to fix the ammunition cartridge.

While the present disclosure has been shown and described with reference to exemplary embodiments thereof, it will be apparent to those of ordinary skill in the art that various changes in form and detail may be made thereto without departing from the spirit and scope of the present disclosure as defined by the following claims.

What is claimed is:

1. A system for inspecting, fixing, or screening ammunition, the system comprising:
   an ammunition conveying track;
   a plurality of ammunition trays arranged on an outer surface of the ammunition conveying track;
   an ammunition inspector disposed at right and left sides of an upper portion of the ammunition conveying track;
   an ammunition fixer disposed downstream of the ammunition inspector at right and left sides of the upper portion of the ammunition conveying track; and
   an ammunition discharger disposed at an end point of the upper portion of the ammunition conveying track, ammunition cartridges being sequentially discharged through the ammunition fixer and the ammunition discharger, wherein at least one of the ammunition inspector and the ammunition fixer includes ammunition-shaped chambers and actuators, wherein the ammunition cartridges placed on the ammunition trays are moved horizontally and inserted into the chambers, and wherein the actuators horizontally move the ammunition cartridges inserted in the chambers back to the ammunition trays, wherein the ammunition inspector includes a plurality of inspecting; chambers and a plurality of inspecting actuators, and the ammunition fixer includes a plurality of fixing chambers and a plurality of fixing actuators, the number of the inspecting chambers being the same as the number of the fixing chambers, and the number of the inspecting actuators being the same as the number of the fixing actuators, and wherein the fixing actuators are operated as per information obtained by the inspecting actuators arranged in the ammunition inspector in the same order as the fixing actuators in the ammunition fixer, wherein the system further comprises an ammunition screener disposed downstream of the ammunition fixer at the right or left side of the upper portion of the ammunition conveying track, wherein the ammunition screener includes a plurality of screening actuators that are of the same number as the inspecting actuators, and wherein the screening actuators are operated as per the information obtained by the inspecting actuators arranged in the ammunition inspector in the same order as the screening actuators in the ammunition screener, wherein the screening actuators are operated as per fixing information obtained by the fixing actuators arranged in the ammunition fixer in the same order as the screening actuators in the ammunition screener wherein the inspecting chambers and the fixing chambers respectively include returning actuators returning inspected or fixed ammunition cartridges to the ammunition trays, and wherein actuating rods of the returning actuators, respectively, push off heads of the ammunition cartridges through the inspecting chambers or the fixing chambers.

2. The system of claim 1, wherein the measurement information is an insertion depth into a particular inspecting chamber corresponding to a particular inspecting actuator, and the fixing information is an operation pressure of a particular fixing actuator or an insertion depth into a particular fixing chamber corresponding to the particular fixing actuator.

\* \* \* \* \*